United States Patent
Zhou et al.

(10) Patent No.: US 11,033,478 B2
(45) Date of Patent: Jun. 15, 2021

(54) MASCARA COMPOSITIONS COMPRISING A POLYMER HAVING CYCLIC AMIDE, CYCLIC AMINE AND ACRYLAMIDE FUNCTIONALITY

(71) Applicant: L'OREAL, Paris (FR)

(72) Inventors: XianZhi Zhou, Millburn, NJ (US); Christopher Pang, New York, NY (US); Jody Ebanks, Bloomfield, NJ (US); Chunhua Li, Hillsborough, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/825,988

(22) Filed: Nov. 29, 2017

(65) Prior Publication Data
US 2019/0159996 A1    May 30, 2019

(51) Int. Cl.
*A61K 8/81*    (2006.01)
*A61Q 1/10*    (2006.01)

(52) U.S. Cl.
CPC .......... *A61K 8/8182* (2013.01); *A61K 8/8158* (2013.01); *A61Q 1/10* (2013.01); *A61K 2800/30* (2013.01)

(58) Field of Classification Search
CPC ................ A61K 8/8182; A61K 8/8158; A61K 2800/30; A61Q 1/10
See application file for complete search history.

(56) References Cited

U.S. PATENT DOCUMENTS

| | | | |
|---|---|---|---|
| 6,214,326 B1 * | 4/2001 | Dupuis | ............... A61K 8/737 424/401 |
| 6,517,823 B1 | 2/2003 | Norman et al. | |
| 7,504,093 B2 | 3/2009 | Bracken et al. | |
| 2007/0224140 A1 | 9/2007 | Quadir et al. | |
| 2012/0237577 A1 | 9/2012 | Sioss et al. | |
| 2012/0327465 A1 * | 12/2012 | Yamada | ................ G06F 21/305 358/1.15 |
| 2016/0175219 A1 * | 6/2016 | Washington | ............ A45D 7/06 132/206 |
| 2017/0035679 A1 | 2/2017 | Douezan et al. | |
| 2017/0065512 A1 | 3/2017 | Zhu et al. | |

FOREIGN PATENT DOCUMENTS

| | | |
|---|---|---|
| EP | 1726331 B1 | 11/2008 |
| EP | 1712255 B1 | 10/2016 |
| WO | 2010014328 A2 | 2/2010 |
| WO | 2017044546 A1 | 3/2017 |

OTHER PUBLICATIONS

"Waterproof Eyebrow Mascara," MINTEL GNPD, record ID 3650969, published Dec. 2015, p. 1-3.
Pro Gel Mascara—database GNPD Mintel www.GNPD.com—ID 4422505 published Nov. 18, 2016, 4 pages.
Mascara—database GNPD Mintel www.GNPD.com ID—990160 published Oct. 22, 2008, 2 pages.
International Search Report and Written Opinion dated Feb. 5, 2019 for corresponding International PCT application No. PCT/US2018/062429 filed Nov. 26, 2018, 10 pages.

* cited by examiner

*Primary Examiner* — Robert S Cabral
(74) *Attorney, Agent, or Firm* — Mike Tyerech; Runzhi Zhao

(57) ABSTRACT

A mascara composition includes at least about 7 percent by weight of a non-ionic water-soluble or water dispersible copolymer that includes a cyclic amide monomer, a cyclic amine monomer, and an acrylamide monomer. Methods of applying makeup to the eyelashes are also provided.

5 Claims, No Drawings

MASCARA COMPOSITIONS COMPRISING A POLYMER HAVING CYCLIC AMIDE, CYCLIC AMINE AND ACRYLAMIDE FUNCTIONALITY

FIELD OF THE INVENTION

The present invention relates to a cosmetic composition for keratinous materials such as keratin fibers. The cosmetic composition is preferably a mascara composition for eyelashes.

DISCUSSION OF THE BACKGROUND

Mascara compositions are commonly used to enhance the appearance of eyelashes. Conventional mascara compositions generally use waxes to form crystalline network structures to enhance curl, volume, length, thickness, and/or colors to eyelashes. However, mascara compositions including large amount of waxes tend to become less resistant to oil and/or sebum, causing smearing, flaking, and/or color transferring after wearing for a certain amount of time. Furthermore, while conventional high wax mascara can be used to assist in moderate curl formation eyelashes, users of mascara typically are forced to rely on particular applicators or eye-lash curling devices to enhance curl to any substantial degree.

The inventors of the present have found that certain mascara formulations are actually useful for inducing a curling effect and lastingness to eyelashes as compared to conventional mascara formulations.

Accordingly, one aspect of the present invention is a mascara composition which is able to impart an enhanced appearance to the eyelashes by enhancing eyelash curling. Another aspect of the present invention is directed to a method of making up eyelashes to enhance physical appearance of the eyelashes.

SUMMARY OF THE INVENTION

According to certain embodiments of the present invention, a mascara composition includes at least about 7 percent by weight of a non-ionic film-forming water-soluble or water dispersible copolymer. The non-ionic, film-forming water-soluble or water dispersible copolymer includes a cyclic amide monomer, a cyclic amine monomer, and an acrylamide monomer. In certain embodiments the mascara composition is substantially free of wax.

According to certain other embodiments of the present invention, a mascara composition includes a vehicle comprising water and a film-forming polymer portion that includes one or more film-forming polymers stabilized in the vehicle. The film-forming polymer portion includes a film-forming polymer that is a non-ionic water-soluble or water dispersible copolymer comprising a cyclic amide monomer, a cyclic amine monomer, and an acrylamide monomer. The mascara composition includes at least about 7 percent by weight of the non-ionic water-soluble or water dispersible copolymer. In certain embodiments the mascara composition is substantially free of wax.

It is to be understood that both the foregoing general description and the following detailed description are exemplary and explanatory only, and are not restrictive of the invention.

DETAILED DESCRIPTION OF THE INVENTION

Unless otherwise indicated, all numbers expressing quantities of ingredients and/or reaction conditions are to be understood as being modified in all instances by the term "about." Accordingly, unless indicated to the contrary, the numerical parameters set forth in the following specification and attached claims are approximations that may vary depending upon the desired properties sought to be obtained by the present invention.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

As used herein, "mascara" and "mascara composition" mean a composition that is intended to be applied to keratinous materials, preferably keratin fibers, in particular eyelashes and/or eyebrows, further in particular eyelashes.

As used herein, "keratinous materials" include, but are not limited to, skin, nail, living keratin fibers such as head hair, eyelashes, and eyebrows, and non-living keratin fibers such as swatches, extensions, and false eyelashes. The living and non-living keratin fibers include any mammalian hair, including human hair.

"Percent" or "%" as used herein, when referring to concentrations of ingredients or components in compositions refers to percent by weight. Unless otherwise specifically stated, the percent of a particular ingredient or ingredients is on a solids basis and is relative to the entire mascara composition.

"Solids basis" or "actives basis" refers to the amount of a particular ingredient exclusive of any solvents, carriers, impurities and the like that may be supplied with the particular ingredient.

"Substantially free" as used herein to refer to the presence of ingredients within compositions of the present invention, means that the particular ingredient is present in concentrations by weight of less than about 1%, such as less than about 0.5%, such as less than about 0.25%, such as about 0%.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The term "self-curling" refers to an attribute associate with compositions of the present invention. Self-curling refers to the ability of a composition to induce curling on eyelashes upon drying—and not from use of an applicator that is specifically to induce curling. Self-curling may be measured using the SELF CURLING TEST noted in this specification.

Mascara Composition

According to the present invention, the inventors have found that particular mascara compositions comprising a film-forming polymer portion and a particulate portion have surprising and unexpected properties such as those related to self-curling. These compositions include a film-forming polymer portion that includes a primary film-forming polymer that is a non-ionic water-soluble or water dispersible copolymer comprising a cyclic amide monomer, a cyclic amine monomer, and an acrylamide monomer. The mascara composition comprises at least about 7 percent by weight of the non-ionic water-soluble or water dispersible copolymer.

Film-Forming Polymer Portion

Mascara compositions of the present invention include a film-forming polymer portion that includes one or more film-forming polymers. One of ordinary skill in the art will readily appreciate the term "film-forming polymer" refers or "film forming agent" as used herein means a polymer or resin that leaves a film (e.g., a continuous film) on the substrate to which it is applied, for example, after a solvent accompanying the film former has evaporated, absorbed into and/or dissipated on or from the substrate. In order to evaluate whether a polymer is a film forming polymer a drawdown test may be performed by putting 5 to 10 grams of material on the center of a Leneta card stock (Black and White Opacity card Chart 2812 available from BYK Additives and Instruments of Geretsried, Germany) and using a 3 mil Drawdown Birdbar (also from Byk), spreading the material for across the sheet (8 in by 3 in) and allowing it to dry overnight. If the material forms a conformal coating and/or can picked up or scraped off with a razorblade to be removed as a free standing film, then it is film forming. Regardless, if it does not coat the card, cannot in any reasonable way be removed as a free-standing film and/or forms a loose powdery coating that rubs off readily onto one's finger, then it is not a film former. Film-forming polymers that are cosmetically or dermatologically acceptable may be utilized in the present invention. As used herein, "cosmetically acceptable" or "dermatologically acceptable" is intended to mean that a composition is suitable for use in contact with human tissues such as keratinous materials and mucous membranes without undue toxicity, incompatibility, instability, and/or allergic response.

The film forming polymer portion includes a film-forming polymer portion that includes a film-forming polymer that is a non-ionic and water-soluble or water-dispersible copolymer comprising a cyclic amide monomer, a cyclic amine monomer, and an acrylamide monomer. Accordingly, the film-forming polymer that is a non-ionic and water-soluble or water-dispersible copolymer comprising a cyclic amide monomer, a cyclic amine monomer, and an acrylamide monomer will have cyclic amide, cyclic amine and acrylamide functionality. For clarity, by "non-ionic and water-soluble or water-dispersible" it is meant that the copolymer is non-ionic. The copolymer is also (either) water-soluble or water-dispersible, particularly to the extent that it can be readily stabilized throughout the vehicle of the composition.

Cyclic amide and cyclic amine monomers useful in film-forming polymers of the present invention include those having one or more aromatic or aliphatic ring structures. These rings may have sizes ranging from about having sizes of, for example, 5 to 8 ring members.

In certain embodiments of the invention, monomers useful in forming the film-forming polymers present in compositions of the present invention are polymerizable ethylenically unsaturated monomers having a cyclic amine residue or a cyclic amide residue. Accordingly, the cyclic amide monomers of the film-forming polymers useful in the present invention may include cyclic amide residues that are or include heterocyclic ring structures such as lactams and the like. These may include α-Lactam, β-lactam, γ-lactam, δ-lactam, and ε-lactam. In one notable embodiment, the cyclic amide is a pyrrolidone (a γ-lactam). Useful cyclic amine residues may include any of various heterocyclic amines such as azoles, pyrroles, pyrrolidines, carbamates, and the like. In one notable embodiment, the cyclic amine residue is an imidazole.

In certain other embodiments, acrylamide monomers useful according to the present invention include those having —$C_3H_5NO$ functional groups. Examples include (meth) acrylamides.

In certain embodiments, the non-ionic, water-soluble or water-dispersible copolymer comprising a cyclic amide monomer, a cyclic amine monomer, and an acrylamide monomer has a weight average molecular weight in a range from about 10,000 daltons to about 1,000,000 daltons.

In certain embodiments, the non-ionic, water-soluble or water-dispersible copolymer comprising a cyclic amide monomer, a cyclic amine monomer, and an acrylamide monomer may be a commercially available variety, such as LUVISET CLEAR AT3, commercially available from BASF of Ludwigshafen, Germany.

The concentration of the non-ionic, water-soluble or water-dispersible copolymer comprising a cyclic amide monomer, a cyclic amine monomer, and an acrylamide monomer in the mascara is greater than about 7%. In certain embodiments the concentration is greater than about 10%, such as greater than about 15%. In certain other embodiments, compositions of the present invention include the non-ionic, water-soluble or water-dispersible copolymer comprising a cyclic amide monomer, a cyclic amine monomer, and an acrylamide monomer in a concentration from about 5%, 10% 15% or 20% to about 20%, 30%, 40% 50% or 60% including all combinations of such ranges.

According to certain embodiments of the invention, the film-forming polymer portion includes a primary film-forming polymer. By "primary film-forming polymer," it is meant the film forming polymer or class thereof that comprises 50% or more of the entire film forming polymer portion. According to certain notable embodiments, the non-ionic, water-soluble or water-dispersible copolymer comprising a cyclic amide monomer, a cyclic amine monomer, and an acrylamide monomer is the primary film forming polymer.

According to certain embodiments the non-ionic, water-soluble or water-dispersible copolymer including a cyclic amide monomer, a cyclic amine monomer, and an acrylamide monomer comprises 55% percent or more by weight of the film-forming polymer portion, such as about 70% or more, such as about 90% of the film-forming polymer portion.

The film-forming polymer portion may also include one or more secondary film-forming polymers. By "secondary" film-forming polymers it is meant that the combined concentration of these one or more secondary film-forming polymers in the mascara composition is less than the concentration of the primary film-forming polymer. The one or more secondary film forming polymers may be any of those that are commonly used in mascara compositions such as non-crosslinked acrylate and acrylic co-polymers, urethane polymers, polyesters. A non-limiting example of a suitable non-crosslinked secondary film-forming polymer is sodium alginate, available as PROTANAL PH 6160 from FMC Health and Nutrition of Philadelphia, Pa. The amount of secondary film-forming polymer (e.g., sodium alginate) present in the mascara composition may be any suitable amount such as in a range from about 0.25% to about 2% by weight.

In certain embodiments of the invention, the secondary film-forming polymer may include additional film-forming polymers that may be stabilized in the vehicle. Suitable additional film-forming polymers include any of various acrylate and acrylic co-polymers, urethane polymers, polyesters and the like that are commonly used in mascara compositions.

Wax

Compositions of the present invention may include wax. As used herein, "wax" is intended to mean a lipophilic fatty compound that is solid at room temperature (about 25° C.) and atmospheric pressure (760 mmHg, i.e., 105 Pa), which undergoes a reversible solid/liquid change of state and which has a melting point of greater than 30° C., and in some embodiments, greater than about 55° C. up to about 120° C. or even as high as about 200° C.

The term wax may include waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, carnauba wax, candelilla wax, ouricurry wax, cork fiber waxes, sugar cane waxes, Japan waxes, sumach wax and cotton wax. Examples of waxes of mineral origin include paraffins, microcrystalline waxes, montan waxes and ozokerites. Examples of waxes of synthetic origin include polyolefin waxes, e.g., polyethylene waxes, waxes obtained by Fischer-Tropsch synthesis, waxy copolymers and their esters, and silicone and fluoro waxes.

The term wax may further include high melting point hydrogenated oils of animal or plant origin. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils.

In certain embodiments, compositions of the present invention include wax, such as from about 0.5%, 2% or 4% to about 5%, 10% or 20% including all combinations of such ranges. However, in certain notable embodiments, compositions of the present invention are substantially free of wax.

Oil

Compositions of the present invention may include oils. However, in certain notable embodiments, compositions of the present invention are substantially free of oils. In certain particular embodiments, compositions of the present invention have less than 0.25% of waxes and less than 0.25% of oils.

As used herein, by "oils," it is meant compounds having a melting point of less than about 30 C and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the oil does not include hydroxyl moieties.

Suitable examples of compounds of oils include vegetable oils (glyceryl esters of fatty acids, triglycerides) and fatty esters. Specific non-limiting examples include, without limitation, esters such as isopropyl palmitate, isopropyl myristate, isononyl isonanoate $C_{12}$-$C_{15}$ alkyl benzoates, caprylic/capric triglycerides, silicone oils (such as dimethicone and cyclopentasiloxane), pentaerythritol tetraoctanoate and mineral oil. Other examples of oils include liquid organic ultraviolet filter commonly used for example as UV-absorbing sunscreens such as octocrylene, octyl salicylate, octyl methoxycinnamate, among others.

In certain embodiments, compositions of the present invention include oils, such as from about 0.5%, 2% or 4% to about 5%, 10% or 20% including all combinations of such ranges. However, in certain notable embodiments, compositions of the present invention are substantially free of oils.

Surfactants and Dispersants

The film-forming polymer portion may provide sufficient thickening of the vehicle to obviate the need for dispersants or suspending agents. However, according to certain embodiments of the present invention, the mascara composition may further optionally include a surfactant or dispersant, primarily to assist in wetting or dispersing of the particulate portion. Any surfactants, including anionic, nonionic, amphoteric, and cationic, surfactants, may be used in the present invention, as long as the surfactant is cosmetically or dermatologically acceptable. The surfactant may be used either singly or in combination two or more thereof. In one embodiment, the mascara composition may include an anionic surfactant/dispersant such as sodium laureth sulfate.

If present, the amount of the surfactant or dispersant may be from about 0.1 to about 5% by weight. In certain other embodiments the concentration of dispersants and surfactants is limited to less than 1%, such as less than about 0.5%, such as less than about 0.1%.

Colorants and Particulates

Mascara compositions of the present invention may optionally include at least one colorant. Suitable colorants include, but are not limited to inorganic particulates that impart color or optical effects and organic pigments. Particulate materials are generally finely divided particulates that are insoluble in but are otherwise homogeneously stabilized (suspended or dispersed) in a vehicle of the composition. The one or more particulate materials are typically materials that are incapable of chemically "self-fusing" in-use and are not themselves film-forming.

Suitable inorganic particulate materials include any of a variety of porous, semi-porous, non-porous, or hollow, coated or uncoated water-insoluble inorganic particulates such as silica, alumina, carbon and any of various oxides, silicates, aluminosilicates, nitrides, carbides, carbonates, and the like. In particular embodiments, the inorganic particulate is selected from carbon black, silica, and iron oxide. Other particulates, e.g., organic pigments such as lake pigments; other organic particulates such as polymeric particulates including nylon particulates, acrylate particulates (e.g., PMMA), silicone elastomer particulates, and the like may also be used.

Any of various lipophilic or water soluble dyes may be used as well. Typically, when the composition contains colorants, the composition may be used as a mascara composition. Alternatively, when the composition does not contain colorants, it is a clear or transparent composition which can be used as a basecoat (or topcoat) prior to (or after) application of a mascara composition to keratinous materials. A composition free of colorants may also be used as a solitary coating (without an additional separate basecoat or topcoat). However, it is possible that topcoats or basecoats could contain colorants, and/or that a mascara composition could contain little or no colorant.

Vehicle

In order to facilitate application to the eyelashes, mascaras of the present invention generally include a vehicle in which the film-forming polymer portion is stabilized (i.e., dissolved, dispersed or suspended). The vehicle generally includes, consists of or consists essentially of water. In certain embodiments of the invention, the mascara compositions of the present invention include at least about 30% water, such as from about 40% to about 90%, such as from about 45% to about 85%.

Additional Ingredients

The mascara composition of the present invention may further include various additives desirably used in cosmetic or dermatological compositions. For example, water, thickeners, dispersants, anti-oxidants, pH adjusters, preservatives, neutralizing agents, fragrances, fillers, co-solvents, plasticizers, cosmetic and dermatological active agents such as emollients, moisturizers, vitamins, UV filters, and sunscreens, and mixtures thereof can be added. A non-exhaustive listing of such ingredients can be found in the CTFA *International Cosmetic Ingredient Dictionary and Handbook*, Fourteenth Edition (2012), contents of which are incorporated herein by reference in its entirety.

One skilled in the art will take care to select the optional additional additives and/or the amount thereof such that the advantageous properties of the mascara compositions according to the present invention are not, or are not substantially, adversely affected by the envisaged addition.

These substances may be selected variously by one skilled in the art to prepare a composition which has the desired properties, for example, consistency or texture.

According to certain embodiments mascaras of the present invention are substantially free of polyhydric alcohols such as glycerin or glycols such as propylene, butylene or hexylene glycol.

According to certain embodiments, the mascara composition of the present invention is in the form of a water solution or dispersion where the non-ionic water-soluble or water dispersible copolymer comprising a cyclic amide monomer, a cyclic amine monomer, and an acrylamide monomer and one or more other ingredients are present as dissolved or dispersed in a vehicle that includes water.

According to certain embodiments mascara compositions of the present invention have a viscosity from about 0.01 kPa·s, 0.1 kPa·s or 0.3 kPa·s to about 0.6 kPa·s, 10 kPa·s or 50 kPa·s including all combinations of such ranges, when measured at a shear rate of 1 s$^{-1}$ as measured using, for example, the AR-G2 magnetic bearing rheometer, available from TA Instruments of New Castle, Del. In order to adjust the viscosity of the mascara formulation, one may use one or more viscosity modifiers. According to certain other embodiments of the invention, the mascara may have a pH that is from about 5 to about 8.

The mascara composition of the present invention is intended to be applied onto keratinous materials such as keratin fibers, in particular, eyelashes or eyebrows. In certain notable embodiments the mascara is applied to a portion of keratinous surface that one desires to adopt a concave curvature. In particular, the inventors have found that compositions of the present invention are useful for self-curling. When used in this regard, the mascara is applied to the top surface of the upper eyelash and allowed to dry. By applying only to the top surface of the lashes, the lash will curl upwards upon drying.

As described above, according to one aspect of the present invention, the mascara composition has improved cosmetic properties such as, for example, increased volume properties, increased self-curling properties, increased self-curl retention properties, increased length properties, and the like.

Methods

Mascara compositions of the present invention may be made by mixing at least one non-ionic, water-soluble or water-dispersible copolymer including a cyclic amide monomer, a cyclic amine monomer, and an acrylamide monomer in water until dissolution. This polymer and other water-soluble ingredients may be mixed by stirring, shaking, grounding, or beating, optionally with a stirrer, a magnetic stirrer, a shaker, a homogenizer, or any other methods suitably used to mix cosmetic composition. The mixing may be carried out with or without heating or cooling the ingredients. Particulates and other ingredients that are to be dispersed are then added with mixing to form a homogeneous mixture.

One embodiment of the present invention provides a method of improving curl of keratinous materials. The mascara composition described above is applied onto the keratinous materials. The keratinous materials are preferably keratin fibers, in particular eyelashes and eyebrows, but especially eyelashes. The mascara composition is applied onto the keratinous materials in an amount sufficient to improve the curl of the keratinous materials. To improve the curl of keratin fibers, the mascara composition may be applied onto the keratin fibers in an amount sufficient to increase the curl, and also a volume and/or length of the keratin fibers. The mascara is applied to a portion of keratinous surface that one desires to adopt a concave curvature, such as the top surface of the upper eyelash and allowed to dry. Accordingly, the mascara compositions may be brushed or applied onto the eyelashes with attentiveness to apply it predominantly on the top surface of the top eyelashes rather than the bottom surface of the top eyelashes.

The way by which the mascara composition is applied onto the keratinous materials is not limited. Preferably, the mascara composition is applied onto keratin fibers by a brush, a wand, or a comb.

The compositions may be applied to eyelashes as needed, preferably once or twice daily, more preferably once daily and then preferably allowed to dry before subjecting to contact such as with clothing or other objects.

Notwithstanding that the numerical ranges and parameters setting forth the broad scope of the invention are approximations, the numerical values set forth in the specific examples are reported as precisely as possible. Any numerical value, however, inherently contain errors necessarily resulting from the standard deviation found in their respective measurements.

Examples Mascara Compositions

Mascara compositions of Inventive Example 1 and Comparative Example 1 were prepared by dissolving varying amounts of LUVISET CLEAR AT3 as shown in Table 1, into a formula that included a fixed amount of SIMULGEL 600 (Seppic, Inc of Fairfield, N.J.), PROTANAL PH 6160, carbon black and water (q.s.).

The following SELF-CURLING TEST was performed on the various compositions. Using a flat iron, hair fiber strands (fake eyelashes), 12 mm in length secured between metal plates—available from SP Equation of Pourcieux, France— were straightened by gently stroking them using a commercially available hair straightener set to 450° F. for a sufficient period to straighten the fibers. Using a tongue depressor, various compositions to be tested were applied to the fake eyelashes and stroked ten times on one side of the simulated eyelashes. This deposits approximately 2 mg to 10 mg of composition. The treated lashes were put into a humidity chamber (25% RH and 32° C.) for 5 minutes. A curl measurement was then taken by placing a protractor near the eyelashes and visually estimating the angle of curl relative to the horizontal surface of the metal plate within which the fake eyelashes are secured.

The result was recorded as Initial Curl. The sample was then placed into a second humidity chamber (60% RH 32 C) for twenty minutes and another assessment was made of the curl as described above. The result was recorded as Curl Retention. The results are shown in Table 3:

TABLE 1

Inventive Examples 1-4

| Example | Concentration by Weight of LUVISET CLEAR AT3[1] | Initial Curl | Curl Retention |
|---|---|---|---|
| 1 | 30% | 5 | 0 |
| 2 | 50% | 25 | 15 |
| 3 | 70% | 25 | 20 |
| 4 | 85% | 60 | 45 |

[1]LUVISET CLEAR AT3 (VP/Methacrylamide/Vinyl imidazole −20% on a solids basis - in water), available from BASF of Ludwigshafen, Germany.

The results indicate that compositions including a non-ionic water-soluble or water dispersible copolymer that includes a cyclic amide monomer, a cyclic amine monomer, and an acrylamide monomer have surprisingly good performance.

What is claimed is:

1. A mascara composition, comprising:
a vehicle comprising water, and
a film-forming polymer portion comprising one or more film-forming polymers stabilized in the vehicle, wherein the film-forming polymer portion comprises a primary film-forming polymer that is a copolymer of N-vinyl pyrrolidone, methacrylamide, and N-vinylimidazole and one or more secondary film-forming polymers, wherein the film-forming polymer portion comprises 55% by weight or more of the copolymer of N-vinyl pyrrolidone, methacrylamide, and N-vinylimidazole, and wherein the mascara composition comprises at least about 15 percent by weight of the copolymer of N-vinyl pyrrolidone, methacrylamide, and N-vinylimidazole.

2. The mascara composition of claim 1 wherein the one or more secondary film-forming polymers comprises sodium alginate.

3. A mascara composition, comprising:
a vehicle comprising water,
a film-forming polymer portion comprising one or more film-forming polymers stabilized in the vehicle, wherein the film-forming polymer portion comprises a primary film-forming polymer that is a copolymer of N-vinyl pyrrolidone, methacrylamide, and N-vinylimidazole and one or more secondary film-forming polymers, wherein the film-forming polymer portion comprises 55% by weight or more of the copolymer of N-vinyl pyrrolidone, methacrylamide, and N-vinylimidazole, and wherein the mascara composition comprises from about 20 percent by weight to about 30 percent by weight of the copolymer of N-vinyl pyrrolidone, methacrylamide, and N-vinylimidazole, and wherein the mascara composition further comprises a colorant.

4. The mascara composition of claim 3 wherein the one or more secondary film-forming polymers comprises sodium alginate.

5. The mascara composition of claim 1, wherein the film-forming polymer portion comprises 70% by weight or more of the copolymer of N-vinyl pyrrolidone, methacrylamide, and N-vinylimidazole.

* * * * *